(12) United States Patent
Ditrich et al.

(10) Patent No.: US 6,713,652 B1
(45) Date of Patent: Mar. 30, 2004

(54) PROCESS FOR HYDROLYZING OPTICALLY ACTIVE AMIDES

(75) Inventors: Klaus Ditrich, Gönnheim (DE); Wolfgang Ladner, Fußgönheim (DE); Johann-Peter Melder, Böhl-Iggelheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/936,348

(22) PCT Filed: Mar. 17, 2000

(86) PCT No.: PCT/EP00/02380
§ 371 (c)(1),
(2), (4) Date: Sep. 11, 2001

(87) PCT Pub. No.: WO00/56699
PCT Pub. Date: Sep. 28, 2000

(30) Foreign Application Priority Data

Mar. 24, 1999 (DE) .......................................... 199 13 256

(51) Int. Cl.[7] .............................................. C07C 209/00
(52) U.S. Cl. ...................... 564/377; 564/386; 564/384; 564/374; 562/588

(58) Field of Search .................................. 564/386, 377, 564/372, 384; 562/588

(56) References Cited

U.S. PATENT DOCUMENTS 5,905,167 A  *  5/1999  Ditrich et al. .............. 562/588

FOREIGN PATENT DOCUMENTS

| WO | 95/08636 | 3/1995 |
| WO | 97/10201 | 3/1997 |

OTHER PUBLICATIONS

Devant & Braun, Chem. Berichte 119, 1986 2197–2207.
White, J. Am. Chem. Soc. 77, 1955 6008.

* cited by examiner

*Primary Examiner*—Samuel Barts
(74) *Attorney, Agent, or Firm*—Keil & Weinkauf

(57) ABSTRACT

The present invention relates to a process for hydrolyzing optically active amides to carboxylic acids and optically active amines with retention of the center of chirality, where the hydrolysis of the amides is carried out with an alkali metal or alkaline earth metal hydroxide in the presence of 5–30% by weight, based on the amide employed, of a polyol or an amino alcohol.

5 Claims, No Drawings

PROCESS FOR HYDROLYZING OPTICALLY ACTIVE AMIDES

The present invention relates to a novel process for cleaving optically active amides.

The hydrolytic cleavage of optically active amides having a center of chilarity in the amine moiety of the molecule can be carried out with retention of the center of chirality only under very elaborate conditions or not at all.

Devant and Braun (Chem. Berichte 119, 2197–2207 (1986)) describe the elimination of chiral amines from acetamides as being impossible without destruction of the center of chirality (page 2194). In addition, the authors find that numerous attempts to hydrolyze the amides to the carboxylic acid and optically active amine under alkaline or acidic conditions were unsuccessful, and that only reaction with dinitrogen tetroxide by the method of White (J. Am. Chem. Soc. 77, 6008 (1955)) gives the desired result. However, this reaction with $N_2O_4$ is complicated and thus unsuitable for industrial processes.

WO 95/08636 describes an enzymatic process for the resolution of racemates of optically active amines, in which the amines are acylated enantioselectively with an ester, then the acylated amine (amide) and unreacted amine in the mixture are separated and, if required, the optically active amine is liberated from the acylated amine (amide) by amide cleavage. However, no process parameters with which the amide cleavage can be carried out are indicated.

WO 97/10201 describes a process for cleaving optically active amides with retention of the center of chirality. In this case, the amides are hydrolyzed with alkali metal or alkaline earth metal hydroxide in the presence of a polyol or amino alcohol. The amount of polyol or amino alcohol used is 10–90, preferably 30–80% of the total weight of the mixture.

It is an object of the present invention to optimize even further the process described in WO 97/10201 in terms of space-time yields, and to reduce the costs of the process.

We have found that this object is achieved by a process for hydrolyzing optically active amides to carboxylic acids and optically active amines with retention of the center of chirality, where the hydrolysis of the amides is carried out with an alkali metal or alkaline earth metal hydroxide in the presence of 5–30% by weight, based on the amide employed, of a polyol or an amino alcohol.

The process according to the invention is suitable for virtually all amides which can be prepared from optically active primary or secondary amines. It is particularly suitable for amides whose amine moiety consists of an optically active arylalkylamines.

It proceeds particularly well with primary arylalkylamines, for example those with the following structures:

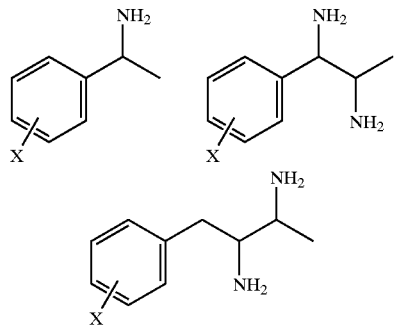

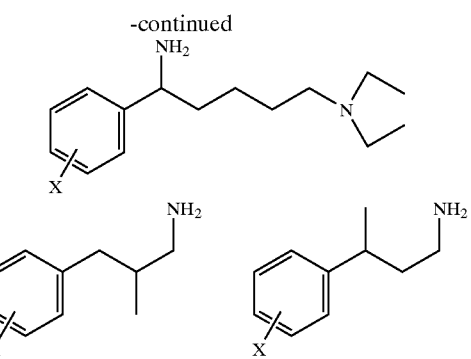

where X is any conventional aromatic substituent, in particular halogen, nitro, cyano, $C_1$–$C_4$-alkyl, $C_1$–$C_4$-alkoxy and $C_1$–$C_4$-alkylthio.

The process according to the invention is also suitable for cleaving amides whose amine moiety consists of an amino alcohol of the formula (I)

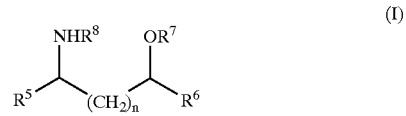

in which the substituents have the following meaning:
$R^5$, $R^6$=independently of one another H, branched and unbranched $C_1$–$C_{10}$-alkyl, $C_1$–$C_4$-alkoxycarbonyl, phenyl, phenyl-$C_1$–$C_4$-alkyl, where the phenyl groups may be substituted by halogen, nitro, cyano, $C_1$–$C_4$-alkyl, $C_1$–$C_4$-alkoxy and $C_1$–$C_4$-alkylthio. It is also possible for $R^5$ and $R^6$ to be connected by a carbon chain which may be interrupted by oxygen, sulfur or nitrogen and in turn may be substituted to form a mono-, bi- or tricyclic system
$R^7$=H, $C_1$–$C_{10}$-alkyl, $C_1$–$C_4$-alkoxycarbonyl
$R^8$=H, $C_1$–$C_{10}$-alkyl
n=0, 1 or 2, preferably 0 or 1.

Where the carbon atoms substituted by $OR^7$ or $NHR^8$ are stereogenic centers, the process according to the invention relates both to the syn and to the anti isomers.

Examples of amino alcohols of the above structure (I) which may be mentioned are:
2-amino-1-butanol; ephedrine; pseudoephedrine; norephedrine; norpseudoephedrine; tert-leucinol; phenylglycinol; 1,2-diphenylaminoethanol; cis- and trans-2-aminocyclopentanol; cis- and trans-1-amino-2-hydroxyindan; cis- and trans-2-aminocyclohexanol, statine, 2-hydroxy-3-aminophenylpropionic acid.

Preferred amino alcohols which may be mentioned are: cis- and trans-1-amino-2-hydroxyindane.

The polyols which can be used in the process according to the invention are glycols, e.g. ethylene glycol and its monoethers e.g. monomethyl glycol.

Further suitable polyols are 1,2-propanediol, 1,3-propanediol, 1,2-butanediol, 2,3-butanediol, 2,4-pentanediol, cis- and trans-cyclohexane-1,2-diol, cis- and trans-cyclohexane-1,4-diol, 2-methyl-2,3-butanediol, 3-methyl-2,4-pentanediol, 2,2-dimethyl-1,3-propanediol, 1-phenyl-1,2-ethanediol, 3-methoxy-1,2-propanediol, 3-phenoxy-1,2-propanediol, 3-butene-1,2-diol, cis- and trans-2-butene-1,4-diol, triethanolamine, triisopropanolamine.

It is also possible to employ polyalkylene glycols, preferably dialkylene glycols and their ethers, in particular diethylene glycol and diglyme, as polyols.

Preferred polyols are ethylene glycol and diethylene glycol.

Suitable amino alcohols for the amide cleavage according to the invention are ethanolamine, diethanolamine and triethanolamine. Triethanolamine is the particularly preferred amino alcohol.

The polyols or amino alcohols should be soluble in water or homogeneously miscible with water. It is also possible to employ mixtures of polyols or amino alcohols.

The polyols are used in an amount of 5–30, preferably 5–20 and, particularly preferably 8–15% of the weight of the amide employed.

Another necessary component in the cleavage according to the invention is an alkali metal or alkaline earth metal hydroxide, in particular sodium or potassium hydroxide. This catalyzes the hydrolysis but is also neutralized by the acid produced, so that it is normally employed in an amount of 1–10 equivalents based on amide.

The hydroxides can advantageously be employed in the form of their aqueous solutions because a certain amount of water is required anyway in the cleavage according to the invention. The amount of water is usually 5–90% of the total weight of solvent. The cleavage according to the invention is preferably carried out at temperatures above 100° C. particularly preferably between 100 and 180° C.

The hydrolysis according to the invention of the amides can be carried out either batchwise or continuously.

It is possible in the continuous procedure to employ, for example, a loop reactor or else a cascade of stirred vessels.

The course of the reaction can easily be followed by conventional methods, for example by gas chromatography.

After the hydrolysis has taken place, the resulting amine is separated and isolated from the carboxylic acid which is in the form of a salt. This preferably takes place be extraction, employing as extractants ethers such as diethyl ether, methyl tert-butyl ether and dibutyl ether, halogenated hydrocarbons such as dichloromethane or trichloroethylene or hydrocarbons such as pentane, hexane, cyclohexane, benzene, toluene and xylene.

A likewise preferred embodiment of the isolation of the amine is steam distillation.

A particularly suitable embodiment of the invention consists of carrying out the cleavage at such a high temperature that the product resulting from the reaction (amine) is distilled out with steam and thus immediately removed from the reaction mixture, whereas the acid, which is in dissociated form under the alkaline conditions, remains where it was.

The process according to the invention can be employed very successfully as one step (step 3) in the process described in WO 95/08636 for resolving racemates of primary and secondary amines. This process comprises the following steps:
1. Reaction of the racemic amines with an ester whose acid component has a fluorine, nitrogen, oxygen, phosphorus or sulfur atom bonded to a carbon atom in the alpha, beta or gamma position relative to the carbonyl carbon atom with specific catalysis by a hydrolase,
2. separation of the enantioselectively acylated amine from the unreacted other enantiomer of the amine,
3. subsequent hydrolysis of the acylated amine.

The esters suitable for this process are those in which electron-rich heteroatom is bonded to a carbon atom in the alpha, beta or gamma position relative to the carbonyl carbon in the acid component of the ester.

The heteroatom can be a fluorine, nitrogen, oxygen, phosphorus or sulfur atom. Oxygen is preferred as heteroatom.

The heteroatom may optionally be linked to other groups, e.g. alkyl groups. If the heteroatom is, for example, oxygen, an ether group is present.

The alcohol component of the ester may consist of branched or unbranched $C_1$–$C_{10}$-alcohols, which may also optionally be substituted.

Particularly suitable alcohol components are 2-propanol, 2-butanol, 2-pentanol, 3-pentanol, 3-methyl-2-butanol, cyclopentanol, cyclohexanol, 2-methylcyclohexanol, 1-chloro-2-propanol, 1-bromo-2-propanol, 4-methyl-2-pentanol, 2,4-dimethyl-3-pentanol, cyclopropylethanol, 1-phenylethanol, 1-phenoxy-2-propanol, 1-methoxy-2-propanol, cis- and trans-2-methoxycyclohexanol, 1-dimethylamino-2-propanol, 1-buten-3-ol, 1-butyn-3-ol, 1-indanol, 2-indanol, 3-hydroxytetrahydrofuran, 5-hydroxy-2-methyl-1,3-dioxane, 4-hydroxypiperidine, (+) and (−)-menthol, (+) and (−)-isomenthol, carveol, lactonitrile, cetone cyanohydrin, benzaldehyde cyanohydrin, pantolactone, t-butyl lactate, acetone 2-hydroxypropyl oxime.

Further suitable alcohol components are 1,2-ethanediol, glycerol, 1,2-propanediol, 1,3-propanediol, 1,2-butanediol, 2,3-butanediol, 2,4-pentanediol, cis- and trans-cyclohexane-1,2-diol, cis- and trans-cyclohexane-1,4-diol, 2-methyl-2,3-butanediol, 3-methyl-2,4-pentanediol, 2,2-dimethyl-1,3-propanediol, 1-phenyl-1,2-ethanediol, 3-methoxy-1,2-propanediol, 3-phenoxy-1,2-propanediol, 3-chloro-1,2-propanediol, 3-bromo-1,2-propanediol, 3-butene-1,2-diol, cis- and trans-2-butene-1,4-diol, triethanolamine, triisopropanolamine.

Particularly suitable esters are those of the structure

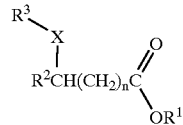

in which
 $R^1$=$C_1$–$C_{10}$-alkyl,
 $R^2$=$C_1$–$C_{10}$-alkyl, H,
 $R^3$=H, $C_1$–$C_{10}$-alkyl, phenyl optionally substituted by $NH_2$, OH, $C_1$–$C_4$-alkoxy or halogen,
 X=O, S, $NR^4$,
 $R^4$=H, $C_1$–$C_{10}$-alkyl, phenyl optionally substituted by $NH_2$, OH, $C_{1-4}$-alkoxy or halogen,
 n=0, 1 or 2.

Among these, the $C_1$–$C_4$-alkyl esters of $C_1$–$C_4$-alkoxyacetic acids, for example of methoxyacetic acid, are preferred. The methyl, ethyl, n-propyl, i-propyl, n-butyl, i-butyl and tert-butyl esters of methoxyacetic acid are very particularly preferred.

A large number of enzymes can be employed as hydrolases in said process. Proteases and, in particular lipases are preferably used. Particularly suitable lipases are microbial lipases which can be isolated, for example, from yeasts or bacteria. Particularly suitable lipases are those from Pseudomonas, e.g.

Amano P, or the lipase from Pseudomonas spec. DSM 8246. Further particularly suitable hydrolases are the enzymes, commercially available from Novo Nordisk (Enzyme Toolbox), in particular the lipases SP 523, SP 524; SP 525, SP 526 and Novozym® 435.

It is also possible and advantageous to employ the lipases "Chirazymes L1 to L8" which are commercially available (Boehringer Mannheim) in the process according to the invention.

The enzyme used can be employed in the native or immobilized form.

The immobilized enzyme Novozym® 435 is particularly suitable.

Suitable solvents are in general organic solvents. The reaction proceeds particularly well in ethers, for example in MTBE or THF, in hydrocarbons such as hexane, cyclohexane, toluene or halogenated hydrocarbons such as methylene chloride.

However, the reaction can also be carried out in the absence of a solvent.

The reaction proceeds particularly well if the solvents and starting materials are if possible in anhydrous form.

The reaction of the ester with the racemic amine or amino alcohol with enzyme catalysis is normally carried out at room temperature. The times for this reaction are from 1 to 48 hours, depending on the substrate and quantity of enzyme. Secondary amines/amino alcohols usually require longer reaction times than do primary amines/amino alcohols. The lower reactivity of secondary amines can also be compensated by increasing the quantity of catalyst relative to primary amines.

From 1 to 6 mol of ester are preferably added per mole of substrate to be reacted, i.e. from 0.5 to 3 mol of ester are required for 1 mol of racemic amine.

The quantity of enzyme to be added depends on the nature of the hydrolase and the activity of the enzyme preparation. The optimal quantity of enzyme for the reaction can easily be determined by simple preliminary tests. As a rule, 1000 units of lipase are added per mmol of amine or amino alcohol.

The progress of the reaction can easily be followed by conventional methods, for example by gas chromatography. In the case of the racemate resolution, it is sensible to terminate the reaction at 50% conversion of the racemic amine or amino alcohol. This usually takes place by removing the catalyst from the reaction vessel, for example by filtering off the enzyme. If the enantioselective amidation is carried out continuously, the enzyme can be retained in a flow-through reactor. The enantioselective reaction of the racemic substrate with the ester results in the corresponding acylated product (amide) from one enantiomer, whereas the other enantiomer remains unchanged. The amine and amide which are then present in the mixture can easily be separated by conventional methods. Extraction or distillation processes are, for example, very suitable for separating the amine and amide in the mixture.

The subsequent cleavage of the optically active amide takes place by the process described above.

The following Examples illustrate the invention.

EXAMPLE 1

Hydrolysis of N-[1-(4-Chlorophenyl)ethyl] methoxyacetamide

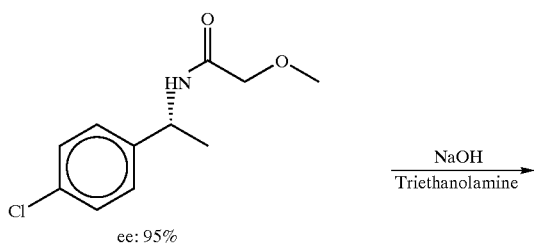

ee: 95%

-continued

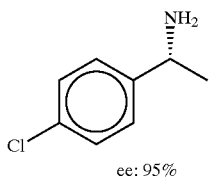

ee: 95%

66 g of amide (0.29 mol) were admixed at 85° C. with 7.3 g of triethanolamine (11% by weight, based on amide) and heated to 120° C. 29.0 g (0.325 mol) of 50% strength sodium hydroxide solution were added, and the reaction mixture was stirred at 115–120° C. for 2 hours and then steam was passed through it. When the distillate was clear, the collected condensate was cooled to room temperature and the lower organic phase was separated off. This crude product was distilled in vacuo. 41.5 g (92%) of R-1-(4-chlorophenyl) ethylamine of boiling point 141–144° C. under 110 mbar were obtained. The optical purity was 95% ee (according to GC).

EXAMPLE 2

Hydrolysis of N-[1-(4-Methylphenyl)ethyl] methoxyacetamide

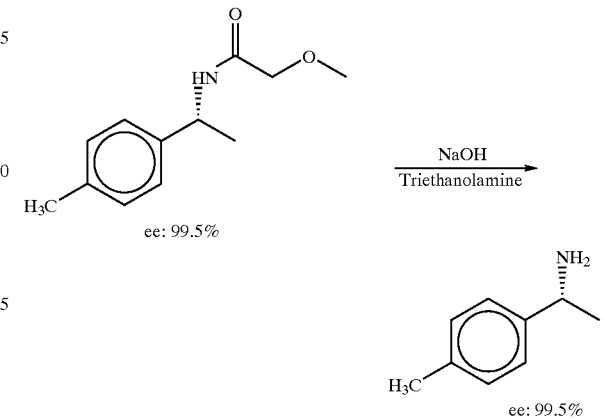

500 g (2.4 mol) of R-N-[1-(4-methylphenyl)ethyl] methoxyacetamide and 50 g of triethanolamine (10% by weight, based on amide) were heated to 115° C., and 290 g (3.6 mol) of 50% strength sodium hydroxide solution were added. The resulting suspension was stirred at 115–120° C. for 4 hours. 250 ml of water were added, and the mixture was allowed to cool to 95° C. and, after addition of 500 ml of toluene, cooled with stirring to room temperature. The phases were separated and the upper organic phase was distilled in vacuo. First an azeotrope of water and toluene distilled, then toluene and finally the product R-1-(4-methylphenyl)ethylamine. 287 g (88%) of amine of boiling point 98° C. under 24 mbar were obtained. The optical purity was 99.5% ee (according to GC).

EXAMPLE 3

Hydrolysis of N-(1-Phenylpropyl)methoxyacetamide

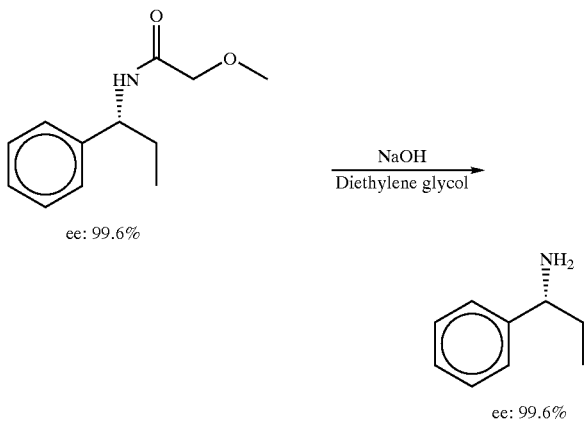

207 g (1 mol) of R-N-(1-phenylpropyl)methoxyacetamide and 50 g of diethylene glycol (24% by weight, based on amide) were heated to 120–130° C., and 104 g (1.3 mol) of 50% strength NaOH were added. The mixture was stirred at 120–130° C. for 5 hours and 90 ml of water and 200 ml of toluene were added. The mixture was allowed to cool with stirring to room temperature, and the phases were then separated. The upper organic phase was distilled in vacuo. Firstly an azeotrope of water and toluene distilled, then toluene and finally the product. 125 g (93%) of R-1-phenylpropylamine of boiling point 126° C. under 111 mbar were obtained. The optical purity was 99.6% ee (GC).

We claim:

1. A process for hydrolyzing optically active amides to carboxylic acids and optically active amines with retention of the center of chirality, where the hydrolysis of the amides is carried out with an alkali metal or alkaline earth metal hydroxide and in the presence of 5–30% by weight, based on the amide employed, of a polyol or an amino alcohol.

2. A process as claimed in claim 1, wherein ethylene glycol, diethylene glycol or triethanolamine is used as polyol.

3. A process as claimed in claim 1, wherein ethylene glycol or diethylene glycol is used as polyol.

4. A process as claimed in claim 1, wherein the hydrolysis is carried out at a temperature above 100° C.

5. A process as claimed in claim 1, wherein the hydrolysis is carried out continuously or batchwise.

* * * * *